(12) United States Patent
Money

(10) Patent No.: US 6,496,734 B1
(45) Date of Patent: Dec. 17, 2002

(54) AUDITORY PROSTHESIS WITH AUTOMATED VOICE MUTING USING THE STAPEDIUS MUSCLE REFLEX

(75) Inventor: David K. Money, New South Wales (AU)

(73) Assignee: Cochlear Limited, New South Wales (AU)

( * ) Notice: Subject to any disclaimer, the term of this patent is extended or adjusted under 35 U.S.C. 154(b) by 0 days.

(21) Appl. No.: 09/556,270

(22) Filed: Apr. 24, 2000

(51) Int. Cl.⁷ ................................................ A61N 1/08
(52) U.S. Cl. ........................................................ 607/56
(58) Field of Search .................................. 600/379, 546, 600/559; 607/55, 56, 57, 137; 623/10

(56) References Cited

U.S. PATENT DOCUMENTS 5,814,095 A  9/1998 Muller et al.
6,157,861 A  * 12/2000 Faltys et al. ................. 607/57

FOREIGN PATENT DOCUMENTS

WO  WO97/48447 A1  12/1997

* cited by examiner

Primary Examiner—George R. Evanisko
Assistant Examiner—Frances P. Oropeza
(74) Attorney, Agent, or Firm—Gottlieb, Rackman & Reisman, P.C.

(57) ABSTRACT

An auditory prosthesis includes a sound sensor that senses both ambient sounds and sounds uttered by the patient. The prosthesis includes a monitor that senses a physiological parameter indicative of the intensity of the sounds as perceived by the patient and/or the onset of a prospective speech episode during which the patient utters sounds. For example, the monitor may detect the activity of the stapedius muscle. This muscle contracts in the presence of subjectively perceived high level sounds or just prior to and during a speech episode. This parameter is used dynamically by the prosthesis to process the received sounds, for example, by changing the amplification level of these sounds dependent on the activity.

26 Claims, 3 Drawing Sheets

AUDITORY PROSTHESIS WITH AUTOMATED VOICE MUTING USING THE STAPEDIUS MUSCLE REFLEX

BACKGROUND OF THE INVENTION

A. Field of Invention

The present invention relates to auditory prostheses, including both cochlear implants and hearing aids More specifically, the present invention pertains to an auditory prosthesis in which the natural stapedius muscle reflex is used to modulate automatically the amplification of the audio channel in the system just prior to, and during an interval when the patient utters sounds, as well as when the patient subjectively perceives loud sounds.

B. Description of the Prior Art

The present invention relates generally to auditory prostheses, such as multi-channel cochlear implants and hearing aids. A cochlear implant conventionally consists of three components—an implanted electrode array, an implanted receiver/stimulator unit (RSU) and an externally worn speech processor (WP). The speech processor receives ambient sound signals, for example, via a microphone, processes them so as to produce a set of signals corresponding to stimuli, and communicates these signals to the RSU. Communication between the speech processor and the RSU may be provided by an inductive link, a direct cable, or any other suitable means. The RSU, in accordance with the received signals, provides electrical stimulation signals to the electrode array.

Since the patient is exposed to various sound levels an AGC feedback circuit is normally used to keep the level of signals within a predetermined relatively constant range. Typically, this circuitry detects an objective or absolute measure of loudness of the ambient sounds, and not the patient's subjective perception of the intensity of these sounds. Therefore a problem associated with present cochlear implant systems is that they do not have the capability of responding to the patient's own subjective perception of sound intensities. This problem is particularly pronounced when a patient starts speaking, because these sounds are subjectively intrinsically louder than ambient sounds but are not treated differently by standard AGC circuitry. This latter situation is somewhat ameliorated by the use in existing systems of unidirectional microphones which are less sensitive to sounds spoken by the patient. However future systems will make use of other schemes, including, for instance, fully implanted systems with implanted microphones. In these fully implanted systems the above mentioned problem will be much more pronounced because implanted microphones are inherently much less directional than the external microphones presently in use and because direct bone conduction will conduct sounds produced by the patient very efficiently to the implanted microphones.

The problem of distinguishing between auditory signals produced by a prosthesis patient and signals produced externally is also present in hearing aids, especially implantable hearing aids. An implantable hearing aid is described, for instance, in U.S. Pat. No. 5,814,095.

The present invention takes advantage of naturally occurring stapedius reflex. This reflex is commonly observed by measuring the acoustic impedance in the middle ear. The acoustic impedance is primarily modulated by the action of the tensor timpani muscle acting on the eardrum, but the action of both the tensor timpani and stapedius muscle is commonly referred to as the stapedius reflex. The following discussion deals with monitoring the stapedius reflex by means of the electrical signal emanating from the stapedius muscle or stapedius nerve. It will be readily understood that the invention can equally be implemented by monitoring the electrical signal emanating from the tensor timpani muscle or tensor timpani nerve.

The stapedius muscle, when contracted, acts as a dampening mechanism on the ossicular chain within the ear. In the normally functioning ear, contraction of the stapedius muscle attenuates the vibration transmitted through the malleus, incus and stapes to the oval window, so as to prevent overstimulation of the auditory system. In a paper by Jerger et al, in Ear and Hearing, vol 9, No 1(1988), entitled "Prediction of dynamic range for the stapedius reflex in cochlear implant patients", amplitude growth functions for an electrically-elicited stapedius reflex were compared with behavioral estimates of dynamic range. This paper concluded that comfort levels are typically greater than or equal to the saturation or plateau level of stapedius response. The stapedius reflex, whilst electrically elicited, was measured using an external acoustic probe arrangement. The onset of the stapedius reflex is conventionally determined in this manner.

It has been found that most people, even candidates for cochlear implants, have a stapedius reflex. As demonstrated above, this reflex is the intrinsic or natural way in which a body protects itself against loud noises. Importantly, it is the same reflex which is also used to suppress a person's perception of his own voice.

It has been suggested that the stapedius reflex be used to determine the stimulation comfort and threshold levels of a patient. See, for instance, commonly assigned PCT publication WO97/09863, corresponding to U.S. application Ser. No. 09/029,365 filed Mar. 4, 1998, entitled DERIVED THRESHOLD AND COMFORT LEVEL FOR AUDITORY PROSTHESIS, now U.S. Pat. No. 6,205,360; and PCT International Publication No. WO97/48447 published on Dec. 24, 1997 and entitled SELF-ADJUSTING COCHLEAR IMPLANT SYSTEM AND METHOD FOR FITTING THE SAME. However in both of these references the stapedius reflex is used only to calculate the above-mentioned parameters while the cochlear implant system is fitted. The references do not suggest the use of the stapedius reflex 'on the fly', i.e., during the normal use of a cochlear system to determine a physiological control parameter indicative of the patient's subjective perception of sound levels, or to detect sounds uttered by or about to be uttered by the patient,

OBJECTIVES AND SUMMARY OF THE INVENTION

The present inventor has discovered that the stapedius reflex is an ideal parameter to measure a person's subjective perception of the loudness or intensity of ambient sounds and that this parameter can be used as a gain control parameter during the normal operation of an auditory prosthesis such as a cochlear implant system or a hearing aid. The present inventor has also discovered that this reflex is an ideal indication of when a patient is speaking since the reflex sets in just before a speaking episode.

It is an object of the present invention to provide an arrangement in which a dynamic physiological parameter indicative of the subjective perception to a patient of sound levels is derived automatically in a prosthesis.

A further objective is to provide an auditory prosthesis in which the stapedius reflex is detected and used to control the output signals generated by the prosthesis.

Yet another objective is to provide an auditory prosthesis in which means are provided to differentiate between sounds generated by the patient and ambient sounds.

A further objective is to provide an implantable auditory prosthesis system which selectively and automatically alters the gain of the system in anticipation of a patient's own voice and subsequent to the resultant utterance.

Yet another objective is to provide an auditory prosthesis system in which the stapedius reflex is used to automatically adjust the system for the perceived loudness of sounds.

Other objectives and advantages of the invention shall become apparent from the following description.

Briefly, the present invention provides an auditory prosthesis which may be, for instance, a cochlear implant including processing means for providing electrical stimulus signals to an implanted stimulation device, said prosthesis including a sensor means adapted to sense the stapedius reflex. The prosthesis also includes a microphone, wherein signals from said microphone are processed by said processing means in accordance with a pre-determined algorithm, so as to define a stimulation sequence to be applied to the patient's auditory nerve. The intensity of the sounds detected by the microphone is monitored and an AGC circuit is used to maintain said intensity in a predetermined range, the output of the AGC circuit being fed to the processing means. A physiological parameter is determined from the sensor means which is indicative of the subjective perception of the patient of said sound intensity. This physiological parameter is used to adjust the operation of the AGC circuit thereby automatically and dynamically compensating for the sound intensity perceived or anticipated by the patient. Preferably this physiological parameter is derived from the stapedius reflex. An advantage of using the stapedius reflex is that physiological parameter derived from it is indicative of loud ambient sounds and it also comprises a precursor for speech uttered by the patient.

In an alternate embodiment, the physiological parameter is fed to the processing means which modifies its operation in the presence of the physiological parameter. For example, signals received by the signal processing means following the stapedius reflex event are processed differently than signals received prior to the stapedius reflex.

The sensor means for the stapedius reflex may include any means which detects either a tightening of the stapedius muscle itself, or a nervous signal associated with the activation of the muscle. A preferred method is to detect electrically the depolarization of the nerve fiber which initiates the contraction leading to the stapedius reflex. Other methods include measuring the electrical signals generated by the stapedius muscle as it contracts, detecting said contraction mechanically, or detecting consequences of the muscular contraction, such as changes in the acoustic impedance of the middle ear. The sensor means may generate a binary signal indicating the activation of the stapedius reflex, or may be multi-valued indicating the intensity of the reflex.

The principles described above are also applicable to a hearing aid as well, including an external hearing aid or fully implanted hearing aid. In an external hearing aid, the amplified signals, attenuated in the present invention in accordance with the signals received from the stapedius reflex monitor, are fed to an output transducer (known as a receiver) inserted into the patient's ear. In a fully implanted hearing aid, the amplified signals are fed to a transducer which transmits corresponding vibrations mechanically to the ossicular chain or directly to the footplate.

BRIEF DESCRIPTION OF THE DRAWINGS

A description of a cochlear implant in accordance with the present invention will now be described with reference to the accompanying figures, in which.

DETAILED DESCRIPTION OF THE INVENTION

Figure 1:
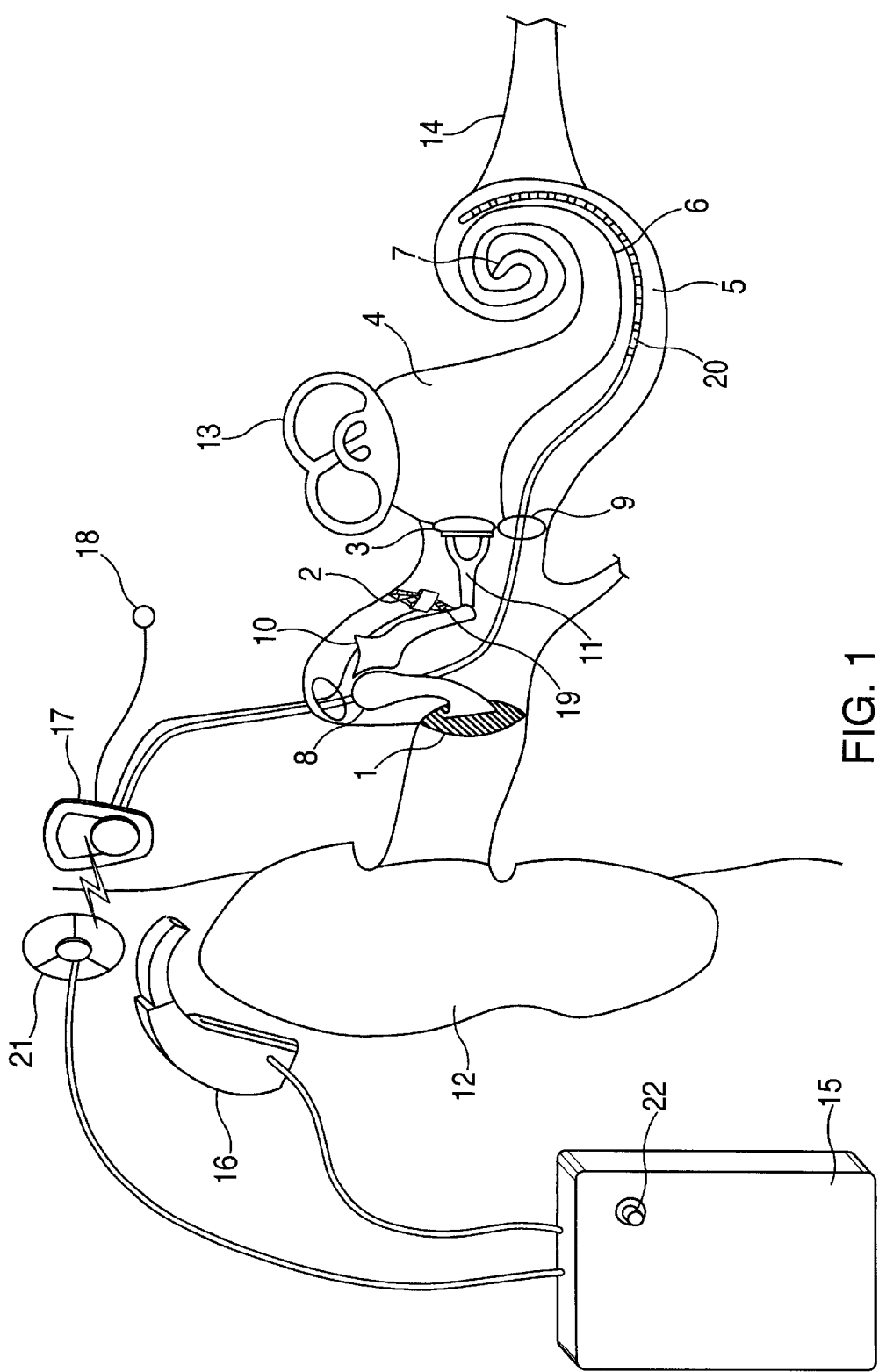
FIG. 1 is a schematic illustration of the implantable cochlear system constructed in accordance with the present invention.

Referring to FIG. 1, the relevant anatomical features of the ear are illustrated. The major portions of the ear include the pinna 12, the tympanic membrane 1, the malleus 8, incus 10, stapedius muscle 2, stapes 11, oval window 3, round window 9, scala timpani 5, scala vestibuli 4, basilar membrane 6, helicotrema 7, labyrinth 13 and auditory nerve 14. In the normally functioning ear, the tympanic membrane 1 vibrates in response to ambient sound, and via the ossicular chain comprising malleus 8, incus 10 and stapes 1, the vibration is transferred to the oval window 3. The stapedius muscle 2 operates in the normal ear to contract and hence damped mechanically the transmission of vibrations to the oval window 3.

An electrode array 20 is shown implanted via conventional surgical procedures, inserted within the scala tympani 5, via the round window 9, and connected to the implanted receiver stimulator unit 17. Receiver stimulator unit 17 communicates via an RF link with RF coil 21, and hence the speech processor 15. A microphone 16, illustratively mounted behind the ear, provides sound signals to the speech processor 15. The implant described to this point is essentially a conventional arrangement.

The stapedius monitoring electrode 19 is attached to the stapedius muscle 2. This provides signals indicative of stapedius reflex activity. It may be attached either to the belly of the muscle or to the tendon which is a surgically easier point of attachment.

Extra-cochlear electrode 18, is used in some conventional stimulation arrangements as the reference electrode for the monopolar stimulation mode, and may also be used as the reference electrode for measuring the evoked action potential of the auditory nerve. In addition, in the present invention it is used in measuring the electrical activity of the stapedius muscle or the stapedius nerve.

The EAP (the evoked action potential) response, detected by the electrode array 20, and the response of the stapedius, monitored by the stapedius monitoring electrode 19, are detected by the receiver stimulator unit 17 relative to the reference electrode, and then telemetered back to the speech processor, using the techniques disclosed, for instance, in U.S. Pat. No. 5,758,651, corresponding to WO94/09863 and incorporated herein by reference.

The neural response evoked by stimulation may be monitored using the implanted electrode array 20. Thus, the implanted array 20 is used both to provide stimuli, and to measure the response to such stimuli during the period between stimuli. The illustrated embodiment may entail using the extracochlear electrode 18 and the intracochlear electrodes of array 20 to monitor the electrical status of the auditory nerve. Both evoked action potential of the auditory nerve and stapedius reflex information are telemetered back from the receiver/stimulator 17 to the wearable speech processor 15. The speech processor 15 includes integral hardware and software to test for comfort and threshold setting levels by using such telemetered information, and applying a predefined algorithm. This enables stimulation levels to be set automatically by the patient by pressing a pushbutton or switch 22, as described in detail in above-mentioned U.S. application Ser. No. 09/029,365, now U.S. Pat. No. 6,205,360, incorporated herein by reference.

It will be appreciated that whilst this division between the processing functions of the receiver/stimulator unit 17 and the speech processor 15 is convenient in terms of current cochlear implant technology, alternative implementations could be used, for example in the case of a fully implantable device as would be understood by one skilled in the art. The location of the processing step is not critical to the general principles of the present invention.

Figure 2:
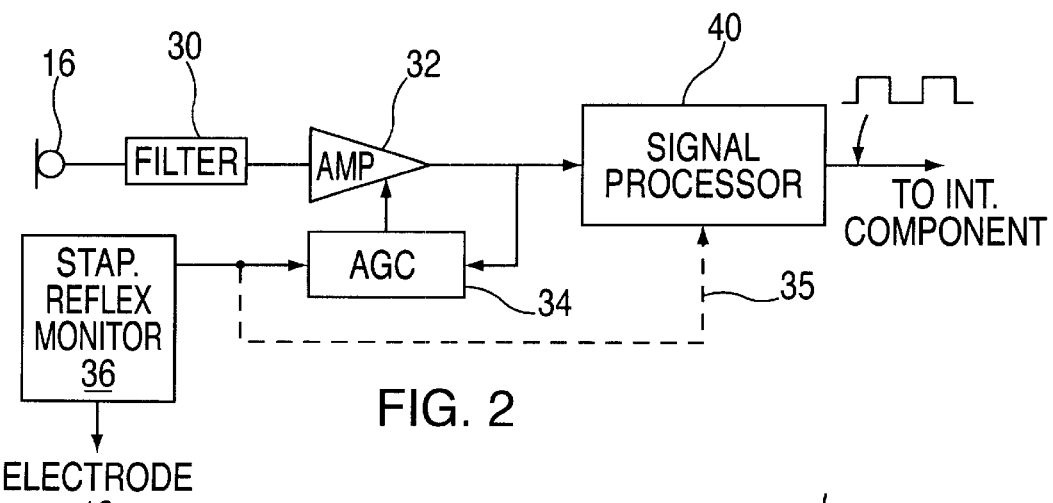
FIG. 2 shows a block diagram of the system of FIG. 1.

Referring now to FIG. 2, the sounds detected by microphone 16 are first filtered by filter 30 and then fed to an amplifier stage 32. The output of the amplifier stage 32 is fed to a speech processor 40 for generating stimulation signals in a normal manner. The signal processor 40 uses an algorithm to generate a sequence of output signals to the internal component.

Figure 3:
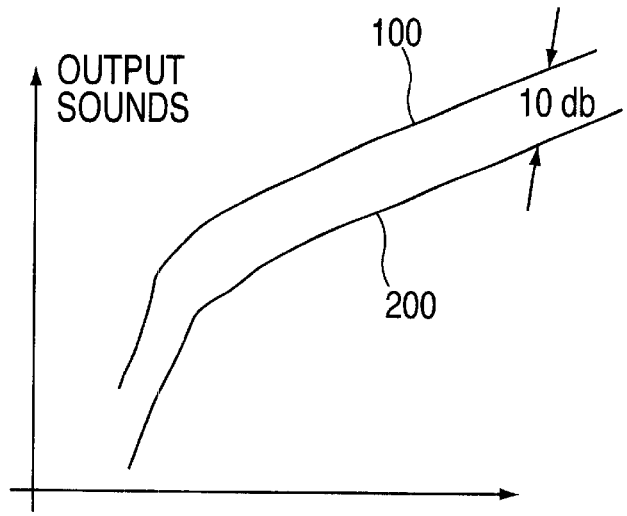
FIG. 3 shows the operation of an automatic gain control circuit for an auditory prosthesis in the presence and absence of a stapedius reflex.

The output of the amplifier stage 32 is also fed to an AGC circuit 34. The AGC circuit 34 is set to reduce the gain of amplifier stage 32 as the level of the sounds sensed by microphone 16 increases, as indicated in FIG. 3 by curve 100. In this manner, the output of the stage 32 can be restricted to within a predetermined range.

Importantly, the AGC circuit 34 also receives an input from the stapedius reflex monitor 36 connected to electrode 19. As discussed above, the electrode 19 generates a stapedius signal indicative of a stapedius muscle contraction and this signal is used by monitor 36 to detect a stapedius reflex. This signal is indicative of either an excessive noise level, as perceived by the patient, or a speech episode (i.e., an episode during which the patient utters sounds). When the AGC circuit 34 receives a signal from the monitor 36, it reduces the gain of the stage 32 uniformly, for example by about 10 to 20 dB, as illustrated in FIG. 3 by curve 200. Alternatively, additional attenuation in the AGC may be added as a graded response to the intensity of the signal from the stapedius reflex monitor (as described more fully below).

In this manner, the amplifier's output is automatically and dynamically reduced in accordance not only with the amplitude of the sounds detected by the microphone 16, but also when the patient either starts speaking or subjectively perceives loud sounds.

In an alternate embodiment of the invention, the stapedius signal from monitor 36 is fed directly to the signal processor 40 to indicate that the stapedius reflex has set in as indicated by dotted connection 35. The processor 40 is constructed and arranged to operate in two modes. A first mode, in the absence of the stapedius signal and in a second mode which may be initiated for a predetermined period after the stapedius reflex has set in. For example, the signal processor 40 may be generating output pulses having an amplitude related to the intensity of the input signals and a pulse width which in the first mode is fixed. In the second mode, the pulse width may be changed to a second value, (if a binary stapedius signal is used) or the pulse width may be modulated in accordance with the stapedius signal (if a multi-valued stapedius signal is used). Of course, pulse width modulation may also be used to indicate the intensity of the sounds and amplitude may be used for the stapedius signal. The 34 output pulses may be further processed in a cochlear device as is well known in the art.

Figure 4:
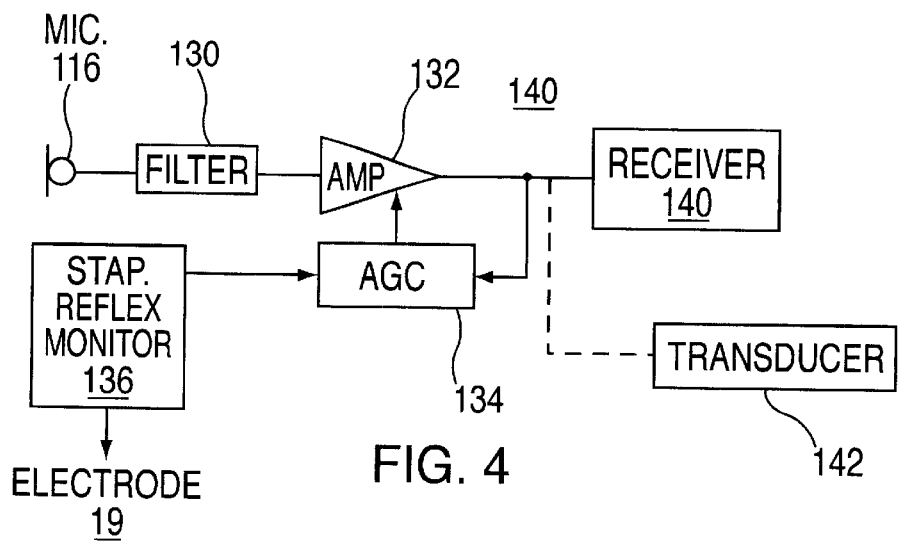
FIG. 4 shows a block diagram of an implantable hearing aid constructed in accordance with this invention.

The invention may also be used in a hearing aid as well. Referring now to FIG. 4, a hearing aid system 110 includes a microphone 116, filter 130, amplifier 132 and receiver 140 (for an external hearing aid). The gain of amplifier 132 is controlled by an AGC 134. Importantly, system 110 also includes a stapedius reflex monitor 136 coupled to an electrode 19.

If system 110 is an implanted hearing aid, the signals from amplifier 132 are fed to a mechanical transducer 142. This mechanical transducer 142 then generates mechanical vibrations to the ossicular chain as described in U.S. Pat. No. 5,814,095 incorporated herein by reference.

Sounds picked up by microphone 116 are filtered, amplified and then reproduced by receiver 140. The gain of amplifier 132 is controlled by the AGC 134 either in accordance with a first curve 100, or in the presence of a signal from the stapedius reflex monitor 136, in accordance with a second curve 200 of FIG. 3. These sounds are then applied to receiver 140, and/or to the mechanical transducer 142.

As mentioned above, the stapedius reflex monitor can determine the stapedius reflex using a number of principles to generate the required stapedius indication signals, including physically sensing the tightening of the stapedius muscle, or by electrically detecting the depolarization of the nerve fibre which initiates the contraction. Other means may include measuring the actual electrical signals generated or emanated by the stapedius muscle as it contracts, or indirectly, by detecting a change in the acoustic impedance of the middle ear. Moreover the monitor 36 (or 136) need not monitor the stapedius muscle ipsilateral with the auditory nerve being stimulated by the electrode array, but instead may be arranged to monitor the stapedius muscle in the contralateral ear.

Figure 5:
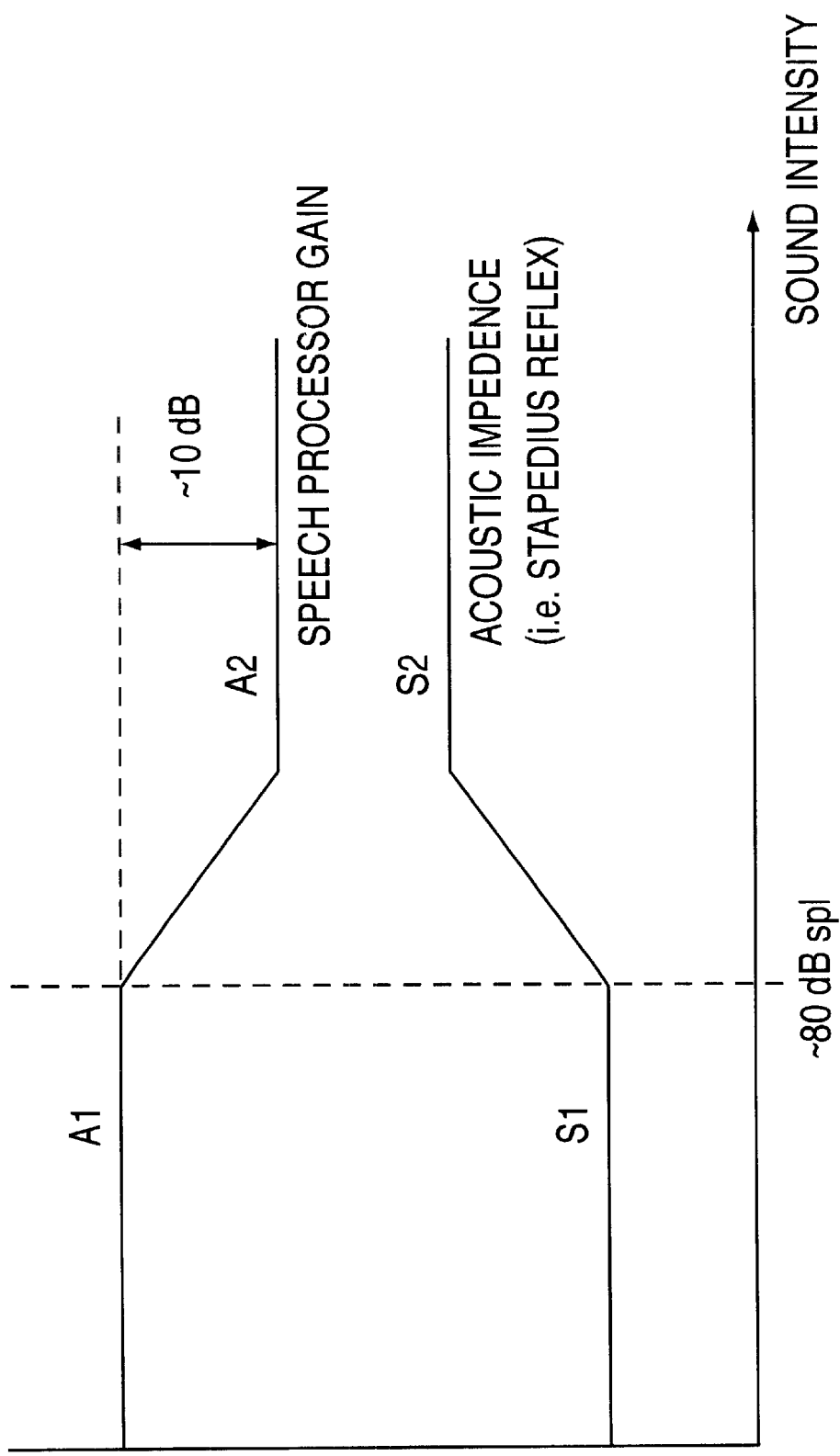
FIG. 5 shows graphically a scheme for setting the gain of an auditory prosthesis with a detector which detects the intensity of the stapedius reflex.

In the embodiments described above, the stapedius reflex monitor 36 (or 136) generates a stapedius signal which is essentially a binary signal indicating either that the reflex is present or is not present. However, the stapedius reflex has a measurable intensity which may be measured by the monitor 36 (or 136) and used to adjust the operation of the processor 15 or hearing aid 110 gradually. For example, as shown in FIG. 5, the gain of amplifiers 32, 132 may be adjusted lineally between the levels A1 and A2 as the stapedius reflex changes between S1 and S2.

Obviously numerous modifications may be made to the invention without departing from its scope as defined in the appended claims.

I claim:

1. An auditory prosthesis system for assisting a patient having hearing organs including a functioning stapedius muscle, said system comprising:
   a sound input receiving sounds and generating corresponding sound signals representative of said sounds;
   an output circuit applying output signals to said patient causing said patient to experience corresponding hearing sensations;
   a stapedius reflex monitor that detects a state of said stapedius muscle and generates a corresponding stapedius signal, said stapedius signal being indicative of one of sound intensities subjectively perceived by said patient and a prospective speech episode during which the patient utters sounds; and
   a signal adjusting circuit that adjusts said sound signals in accordance with said stapedius signal to generate said output signals said signal adjusting circuit including an amplifier having a gain and receiving said sound signals, said amplifier being adapted to generate corresponding amplified signals, said output signals corresponding to said amplified signals, and an automatic gain control circuit that adjust said gain dynamically in accordance with said stapedius signal.

2. The system of claim 1 wherein said automatic gain control circuit receives said amplified sound signals and generates a first gain for said amplifier in the absence of said stapedius signal and a different gain in the presence of said stapedius signal.

3. The system of claim 2 wherein said different gain is lower than said first gain whereby said output signals are amplified less in the presence of said stapedius signal.

4. The system of claim 1 wherein said stapedius reflex monitor includes a sensor arranged to sense a mechanical contraction of said muscle.

5. The system of claim 1 wherein said stapedius reflex monitor includes a sensor electrode arranged to sense an evoked action potential from said stapedius muscle or stapedius nerve.

6. The system of claim 1 wherein said gain control circuit is adapted to select said gain from one of a first gain curve corresponding to the absence of said stapedius reflex and a second curve corresponding to the presence of said stapedius reflex.

7. The system of claim 1 wherein said prosthesis is a hearing aid, and wherein said output circuit includes a receiver generating sound corresponding to said amplified signals.

8. The system of claim 7 wherein said prosthesis is an implantable hearing aid.

9. The system of claim 1 wherein said prosthesis is a cochlear implant including a speech processor that generates stimulation signals and an output electrode that applies said stimulation signals to an auditory nerve of said patient.

10. The system of claim 9 wherein said cochlear implant is completely implantable.

11. The system of claim 1 wherein said prosthesis is completely implantable.

12. An implantable cochlear system for implantation into a patient, said system comprising:
   a sound receiver receiving ambient sounds and sounds generated by said patient;
   a processor that processes said sounds to generate stimulation signals;
   an output electrode that delivers said stimulation signals to an auditory nerve; and
   a stapedius reflex monitor that monitors a state of the stapedius muscle of said patient to identify an onset of a prospective speech episode during which sounds are uttered by the patient and generating a corresponding stapedius signal;
   wherein said processor includes an amplifier with a variable gain, said gain being modified in response to said stapedius signal.

13. The system of claim 12 wherein said processor includes a gain control circuit coupled to said stapedius reflex monitor, said gain control circuit setting gain to a first value for ambient sounds and a different value during said speech episode.

14. The system of claim 12 wherein said stapedius reflex monitor is arranged to identify an activity by said stapedius muscle.

15. The system of claim 12 wherein said patient has a first ear and a second ear with said first ear being associated with said auditory nerve and said stapedius muscle.

16. The system of claim 12 wherein said patient has a first ear and a second ear and wherein said auditory nerve is associated with said first ear while said stapedius muscle is associated with said second ear.

17. The system of claim 12 wherein said stapedius muscle contracts mechanically prior to said speech episode and wherein said stapedius reflex monitor is arranged to sense said mechanical contraction.

18. The system of claim 12 wherein said stapedius muscle is associated with a stapedius nerve generating an electrical signal associated with a contraction of said stapedius muscle and wherein said monitor includes a sensor electrode arranged to detect said electrical signal.

19. An auditory prosthesis designed to aid a person with a hearing impairment and having an intact stapedius reflex, said auditory prosthesis comprising:
   a sound receiver adapted to receive sounds and to generate corresponding electrical signals;

a monitor adapted to detect said stapedius reflex as an indication of at least one of a subjective perception of the intensity of ambient sounds by the patient and a prospective speech episode during which the patient utters sounds, and to generate an indication signal when said physiological parameter is detected;

a signal processor adapted to process said electrical signals in a first mode in the absence of said indication signal and a different mode in the presence of said indication signal to generate output signals.

20. The prosthesis of claim 19 wherein said signal processor includes a variable gain amplifier and a gain adjusting circuit adapted to set the gain of said amplifier, said gain adjusting circuit generating a first gain in the absence of said indication signal, and a different gain in the presence of said indication signal.

21. The prosthesis of claim 20 wherein said monitor generates said indication signal to indicate a level of activity of said stapedius reflex and wherein said gain adjusting circuit selects said different gain based on said stapedius signal.

22. The prosthesis of claim 19 wherein said signal processor generates output signals having a pulse width, said processor determining a first pulse width for said output signals when no stapedius reflex is detected and a different pulse width after said stapedius reflex is detected.

23. A hearing aid for stimulating a patient's hearing organs, comprising;
   a sound receiver receiving sounds and converting them into electrical signals;
   an amplifier with a gain amplifying said electrical signals to generate amplified signals;
   an output element that applies said amplified signals to the patient's hearing organs;
   a stapedius reflex monitor that monitors the stapedius reflex of the patent; and
   a gain control circuit coupled to said stapedius reflex monitor controlling said gain to set said amplifier to one of a normal gain and a different gain dependent on a stapedius reflex monitor output.

24. The hearing aid of claim 23 wherein said stapedius reflex monitor generates a stapedius signal indicative of a level of said stapedius reflex and wherein said gain control circuit includes a gain adjusting circuit adapted to select said different gain to a value dependent on said stapedius signal.

25. The hearing aid of claim 23 wherein said output element comprises a receiver.

26. The hearing aid of claim 23 wherein said output element comprises a transducer, that generates mechanical vibrations corresponding to said amplified signals.

* * * * *